US012594240B2

(12) United States Patent
Altenburger et al.

(10) Patent No.: US 12,594,240 B2
(45) Date of Patent: Apr. 7, 2026

---

(54) ARTIFICIAL VITREOUS HUMOR FOR THE INVESTIGATION OF DRUGS AND DRUG FORMULATIONS

(71) Applicant: Hoffmann-La Roche Inc., Little Falls, NJ (US)

(72) Inventors: Ulrike Altenburger, Lörrach (DE); Sulabh Pravinchandra Patel, Basel (CH); Gregoire Schwach, Neuchatel (CH); Pankaj Shende, Maharashtra (IN)

( * ) Notice: Subject to any disclaimer, the term of this patent is extended or adjusted under 35 U.S.C. 154(b) by 0 days.

(21) Appl. No.: 18/298,991

(22) Filed: Apr. 11, 2023

(65) Prior Publication Data

US 2024/0074972 A1 Mar. 7, 2024

Related U.S. Application Data

(63) Continuation of application No. 16/855,893, filed on Apr. 22, 2020, now abandoned, which is a continuation of application No. PCT/EP2018/078937, filed on Oct. 23, 2018.

(30) Foreign Application Priority Data

Oct. 25, 2017 (EP) ..................................... 17198210

(51) Int. Cl.

| | |
|---|---|
| *A61K 9/08* | (2006.01) |
| *A61K 47/02* | (2006.01) |
| *A61K 47/18* | (2017.01) |
| *A61K 47/26* | (2006.01) |
| *A61K 47/36* | (2006.01) |
| *A61K 47/42* | (2017.01) |

(52) U.S. Cl.
CPC ................ *A61K 9/08* (2013.01); *A61K 47/02* (2013.01); *A61K 47/183* (2013.01); *A61K 47/26* (2013.01); *A61K 47/36* (2013.01); *A61K 47/42* (2013.01)

(58) Field of Classification Search
CPC ......... A61K 9/08; A61K 47/26; A61K 47/183
See application file for complete search history.

(56) References Cited

U.S. PATENT DOCUMENTS

| | | | |
|---|---|---|---|
| 4,716,154 A | 12/1987 | Malson et al. |
| 8,277,830 B2 | 10/2012 | de Juan et al. |
| 8,298,578 B2 | 10/2012 | de Juan et al. |
| 8,399,006 B2 | 3/2013 | de Juan et al. |
| 8,623,395 B2 | 1/2014 | de Juan et al. |
| 8,795,712 B2 | 8/2014 | de Juan et al. |
| 8,808,727 B2 | 8/2014 | de Juan et al. |
| 8,905,963 B2 | 12/2014 | de Juan et al. |
| 9,033,911 B2 | 5/2015 | de Juan et al. |
| 9,066,779 B2 | 6/2015 | de Juan et al. |
| 9,417,238 B2 | 8/2016 | Reich et al. |

| | | | |
|---|---|---|---|
| 9,492,315 B2 | 11/2016 | de Juan et al. |
| 9,851,351 B2 | 12/2017 | Reich et al. |
| 9,861,521 B2 | 1/2018 | de Juan et al. |
| 10,166,142 B2 | 1/2019 | de Juan et al. |
| 10,265,215 B2 | 4/2019 | de Juan et al. |
| 10,656,152 B2 | 5/2020 | de Juan et al. |
| 10,813,788 B2 | 10/2020 | de Juan et al. |
| 11,642,310 B2 | 5/2023 | de Juan et al. |
| 11,786,396 B2 | 10/2023 | de Juan et al. |
| 2004/0087671 A1 | 5/2004 | Tamada et al. |
| 2008/0129961 A1 | 6/2008 | Schwartz et al. |
| 2010/0255061 A1 | 10/2010 | de Juan et al. |
| 2011/0200676 A1 | 8/2011 | Lin et al. |
| 2012/0029445 A1 | 2/2012 | de Juan et al. |
| 2012/0029470 A1 | 2/2012 | de Juan et al. |
| 2012/0087891 A1 | 4/2012 | Gorkovenko et al. |
| 2012/0095439 A1 | 4/2012 | de Juan et al. |
| 2013/0204209 A1 | 8/2013 | de Juan, Jr. et al. |
| 2013/0245544 A1 | 9/2013 | de Juan et al. |
| 2013/0245573 A1 | 9/2013 | de Juan et al. |
| 2013/0324918 A1 | 12/2013 | de Juan et al. |
| 2013/0324942 A1 | 12/2013 | de Juan et al. |
| 2014/0045951 A1 | 2/2014 | Uesugi et al. |
| 2014/0073714 A1 | 3/2014 | Reich et al. |
| 2014/0121609 A1 | 5/2014 | de Juan et al. |
| 2014/0358125 A1 | 12/2014 | de Juan et al. |
| 2015/0250647 A1 | 9/2015 | de Juan et al. |

(Continued)

FOREIGN PATENT DOCUMENTS

| | | |
|---|---|---|
| CN | 101934089 A | 1/2011 |
| CN | 102049067 A | 5/2011 |

(Continued)

OTHER PUBLICATIONS

Kummer et al (Proceeding of the 29th Annual International Conference of the IEEE EMBS, Lyon, France, Aug. 23-26, 2007, pp. 6406-6409) (Year: 2007).*
Everett Kinsey (Circulation, Ion Movement in the Eye, vol. XXI, May 1960) (Year: 1960).*
Shapiro et al (Retina Today, Oct. 2015, https://retinatoday.com/articles/2015-oct/vitreous-substitutes) (Year: 2015).*
Stein et al (Current Directions in Biomedical Engineering, 2015, vol. 1, pp. 236-239) (Year: 2015).*
Mulla (Role of Vitreous Humor Biochemistry in Forensic Pathology, 2005, Graduate Thesis from University of Saskatchewan, Saskatoon, Saskatchewan) (Year: 2005).*
Ankamah et al (Antioxidants (Basel), 2020, vol. 9, pp. 1-20) (Year: 2020).*
Sobolewska et al (International Journal of Retina Vitreous, Jun. 2017, vol. 3, pp. 1-6) (Year: 2017).*
Patel et al (Supplementary Information, European Journal of Pharmaceutics and Biopharmaceutics, Mar. 2017 (epub Nov. 16, 2016), vol. 112, 2017 (Year: 2017).*

(Continued)

*Primary Examiner* — Mark V Stevens
(74) *Attorney, Agent, or Firm* — Hoffmann-La Roche Inc.

(57) ABSTRACT

The invention relates to an artificial vitreous humor composition comprising a phosphate buffer, wherein the phosphate buffer has a pH value in the range from 7.0 to 7.7, particularly from 7.1 to 7.6, more particularly from 7.2 to 7.5. The invention further relates to a method of production of an artificial vitreous humor composition, a method for analyzing the behavior of a substance, a method for analyzing the change of the artificial vitreous humor composition upon contact with a substance and a kit of parts.

5 Claims, 9 Drawing Sheets

(56) References Cited

U.S. PATENT DOCUMENTS

| | | | |
|---|---|---|---|
| 2015/0297402 A1 | 10/2015 | de Juan et al. | |
| 2016/0101046 A1 | 4/2016 | Reich et al. | |
| 2018/0161202 A1 | 6/2018 | de Juan et al. | |
| 2018/0292403 A1 | 10/2018 | de Juan et al. | |
| 2019/0336335 A1 | 11/2019 | de Juan et al. | |
| 2021/0025885 A1 | 1/2021 | de Juan et al. | |
| 2021/0196510 A1 | 7/2021 | de Juan et al. | |

FOREIGN PATENT DOCUMENTS

| | | | |
|---|---|---|---|
| CN | 102365109 A | 2/2012 |
| CN | 102762647 A | 10/2012 |
| CN | 103501828 A | 1/2014 |
| EP | 0185070 A1 | 6/1986 |
| EP | 0185070 B1 | 6/1986 |
| EP | 1600778 A1 | 11/2005 |
| EP | 2540284 A2 | 1/2013 |
| JP | S61-502310 A | 10/1986 |
| WO | 86/00079 A1 | 1/1986 |
| WO | 2008/067525 A2 | 6/2008 |
| WO | 2018/088548 A1 | 8/2010 |
| WO | 2012/019136 A2 | 2/2012 |

OTHER PUBLICATIONS

Ankamah, E., et al., "Vitreous Antioxidants, Degeneration, and Vitreo-Retinopathy: Exploring the Links" Antioxidants (Basel) 9(1):7 (1-20) (Dec. 20, 2019).

ATT Bioquest, "PBS (Phosphate Buffered Saline) (1X, pH 7.4) Preparation and Recipe" ATT Bioquest (General Preparation Guidelines), : 1-3 ( 2019) https://www.aatbio.com/resources/buffer-preparations-and-recipes/pbs-phosphate-buffered-saline.

Azzolini, C., et al., "Interactions Between Light and Vitreous Fluid Substitutes" Arch Ophthalmol-Jama 110(10):1468-1471 (Oct. 1, 1992).

Conway, M. et al., "Buffering capacity of bovine vitreous" Retina 28(1):150-153 (Jan. 1, 2008).

Greiner, J.V., et al., "Comparison of phosphate metabolites of the ocular humors" Ophthalmic Res 23(2):92-97 (Jan. 1, 1991).

"International Preliminary Report on Patentability—PCT/EP2018/078937" (Report Issuance Date: Apr. 28, 2020),:pp. 1-8 (May 7, 2020).

"International Search Report—PCT/EP2018/078937" (w/Written Opinion),:pp. 1-14 (Jan. 23, 2019).

Kasdorf, B., et al., "Diffusion Regulation in the Vitreous Humor" Biophys J. 109(10):2171-2181 (Nov. 17, 2015).

Kinsey, E.,, "Ion Movement in the Eye" Circulation 21(5):968-987 (May 1, 1960).

Kleinberg, T., et al., "Vitreous substitutes: a comprehensive review" Survey of Ophthalmology 56(4):300-323 (Aug. 1, 2011).

Koyama, R., et al., "Catalogue of soluble proteins in human vitreous humor by one-dimensional sodium dodecyl sulfate-polyacrylamide gel electrophoresis and electrospray ionization mass spectrometry including seven angiogenesis-regulating factors" J Chromatogr B Analyt Technol Biomed Life Sci 792(1):5-21 (Jul. 15, 2003).

Mulla, A.,, "Role of Vitreous Humor Biochemistry in Forensic Pathology" University of Saskatchewan—CA (Graduate Thesis—Masters Pathology),: 1-165 (Jul. 1, 2005).

Patel, S., et al., "Evaluation of protein drug stability with vitreous humor in a novel ex-vivo intraocular model" Eur J Pharm Biopharm 95( Suppl Part B):407-417 (Sep. 1, 2015).

Patel, S., et al., "Prediction of intraocular antibody drug stability using ex-vivo ocular model" Eu J Pharm Biopharm 112:177-186 (Mar. 1, 2017).

Patrick, W., et al., "Free amino acid content of the vitreous humour in cot deaths" Arch Dis Child 63(6):660-662 (Jun. 1, 1988).

Shapiro, A., et al., "Vitreous Substitutes" Retina Today:1-2 (Oct. 1, 2015) https://retinatoday.com/articles/2015-oct/vitreous-substitutes.

Sobolewska, B., et al., "pH of anti-VEGF agents in the human vitreous: low impact of very different formulations" Int J Retina Vitreous 3(22):45 (1-6) (Oct. 16, 2017).

Upadhyaya, B., et al., "Expression and distribution of thiol-regulating enzyme glutaredoxin 2 (GRX2) in porcine ocular tissues" Exp Eye Res 130:58-65 (Jan. 1, 2015).

Anonymous, "Phosphate-buffered saline (PBS)" Cold Spring Harbor Protocols 2006(1) (Jun. 2, 2006): Retrieved from the Internet: URL: https://dx.doi.org/10.1101/pdb.rec8247.

Anonymous, "10x PBS pH 7.4, Catalog # AM9624-AM9625" (Feb. 1, 2008), pp. 1-1, https://www.thermofisher.com/document-connect/document-connect.html?url=https://assets.thermofisher.com/TFS-Assets%2FLSG%2Fmanuals%2Fsp_9625.pdf.

* cited by examiner

Sampling port

Protein formulation

Buffer
(12 ml)

VH
(4 ml)

Diffusion controlling membrane (50kDa)

Artificial VH

Protein formulation

☒PBS + mAb (ExVit)    ☒pVH + mAb (ExVit)
☒aVH + mAb (ExVit)    ☒aVH + mAb (Vial)

☒PBS + mAb (ExVit)    ☒pVH + mAb (ExVit)
☒aVH + mAb (ExVit)    ☒aVH + mAb (Vial)

ARTIFICIAL VITREOUS HUMOR FOR THE INVESTIGATION OF DRUGS AND DRUG FORMULATIONS

CROSS REFERENCE TO RELATED APPLICATIONS

This application is a continuation of U.S. patent application Ser. No. 16/855,893, filed Apr. 22, 2020, which is a continuation of International Application No. PCT/EP2018/078937, filed Oct. 23, 2018, which is claims benefit of priority to European Patent Application No. 17198210.1, filed Oct. 25, 2017, which are incorporated herein by reference in its entirety.

FIELD OF THE INVENTION

The invention relates to artificial vitreous humor compositions, a method for the production of an artificial humor, a method for analyzing the behavior of a substance and a kit of parts.

BACKGROUND

For the treatment of macular degeneration or retina diseases such as for example diabetic retinopathy, intravitreal injections of drugs have proven successful. In intravitreal injections a drug formulation is directly injected into the vitreous humor (VH), that is, the clear gel filling the space between lens and retina of the eyeball of for example humans. The fraction of an administered dose of an unchanged drug that reaches the retina is high, thus intravitreal injections usually have high bioavailability.

However, in-vitro tests to study for example stability of a drug formulation in VH have proven little useful when simulating real in vivo conditions. VH, when not in its natural environment, degenerates fast and the pH value of VH may increase rapidly due to accumulation of degenerated products in the VH. Thus, tests may not represent the actual situation in an eye of a living subject, especially not over long periods of time, e.g. several days. In more advanced test systems, the physiological pH value of VH may be stabilized by applying a buffering system. Therein, degradation products are allowed to leave the VH through a semi-permeable membrane into a buffer solution.

Following intravitreal (IVT) injection of a drug formulation or a drug-loaded long acting delivery (DDS) system (E. P. Holowka, S. K. Bhatia, Controlled release systems, Drug Delivery: Materials Design and Clinical Perspective, Chapter-2, Springer Science Business Media, New York, 2014, ISBN: 978-1-4939-1997-0, 7-62.), the therapeutic agent remains in the VH and gets exposed at physiological pH and temperature for significantly longer duration. Therefore, it is of prime interest to study the stability of these agents in VH at physiological conditions. Physical and chemical variability of the natural human VH is accounted from disease condition and age, which may have direct impact on the stability predictions. When VH of animal origin is used (e.g. rabbit, pig, monkey or others), there are significant biological intra- and inter-species variabilities e.g. relating to variabilities in viscosity and/or density.

It is known that the natural VH is composed of various small and large inorganic and organic molecules which can be largely categorized as buffer system, small molecular weight components (e.g. salts and ions) and matrix forming polymers (e.g. collagen and hyaluronic acid). In detail natural VH is largely composed of water (98-99%). The remaining constituents (1-2%) are mainly collagen, hyaluronic acid, proteins and small molecular weight components such as ascorbic acid, glutathione, glucose, lactate, xanthine, hypoxanthine, creatinine and urea as disclosed in Kleinberg et al. (Vitreous substitutes: a comprehensive review, Surv Ophthalmol. 2011 July-August; 56(4): 300-23) and Amith Mulla (Role of vitreous humor biochemistry in forensic pathology, University of Saskatchewan, Thesis, 2005).

There is a need to solve the aforementioned challenges by developing an artificial vitreous humor (aVH), which is able to offer better control over the physical and chemical parameters, and improves robustness of the investigation. This is achieved by the featurese of the independent claims.

SUMMARY OF THE INVENTION

We have evaluated novel compositions of aVH comprising a buffer system, small molecular weight (SMW) components and large molecular weight (LMW) components such as matrix forming polymers, which can then serve as an in-vitro model for the prediction of drug or drug formulation stability, and drug release behavior from DDS systems following IVT delivery. The novel aVH would prove as the simplest yet very efficient real-time in-vitro experimental medium for stability and release prediction. Hence, the novel aVH compositions as described herein may serve as research tool but also as quality control tool. According to a first aspect of the invention, an artificial vitreous humor composition is provided comprising a phosphate buffer. The phosphate buffer has a pH value in the range from 7.0 to 7.7, particularly from 7.1 to 7.6, more particularly from 7.2 to 7.5. Most particularly the phophate buffer has a pH value of 7.4. The phosphate buffer may be selected from the group consisting of phosphate buffer saline (PBS), phosphate buffer saline inlcuding Tween (PBST), phosphate buffer saline inlcuding Tween and sodium azide (PBSTN) and phosphate buffer saline including sodium azide (PBSN).

The phosphate buffer may be phosphate buffer saline (PBS). The phophate buffer saline may be in the range particularly from 0.001 to 0.2 M, more particularly from 0.003 to 0.05, most particularly from 0.005 to 0.02 M. The phophate buffer saline preferably has a pH value of 7.4. A preferred buffer according to the invention is 0.01 M PBS, pH 7.4 comprising 8 gm/L NaCl, 0.2 gm/L KCl, 1.44 gm/L $Na_2HPO_4$ and 0.24 gm/L $KH_2PO_4$.

The artificial vitreous humor composition may comprise at least one small molecular weight component. The small molecular weight component may be selected from the group consisting of creatinine, glucose, urea, xanthine, hypoxanthine, sodium lactate and glutathione. The artificial vitreous humor composition may comprise at least one of up to 578 μM creatinine, up to 28.1 mM glucose, up to 58.5 mM urea, 200 to 1630 μM xanthine, 100 to 800 μM hypoxanthine, 0.1 to 23 mM sodium lactate, 50 to 300 μM glutathione. In a preferred embodiment, the artificial vitreous humor composition comprises 64.6 μM creatinine, 2.2 mM glucose, 7.6 mM urea, 580 μM xanthine, 309 μM hypoxanthine, 10.5 mM sodium lactate and 200 μM glutathione.

Furthermore, the artificial vitreous humor composition may comprise 20 to 300 mg/L type II collagen and/or 0.03 to 0.9% w/v sodium hyaluronate. Collagen and/or sodium hyaluronate serve as matrix forming components in the artificial vitreous humor. In a preferred embodiment of the invention the artificial vitreous humor compositions comprises 40 mg/L type II collagen and/or 0.6% w/v sodium hyaluronate.

The artificial vitreous humor composition may not comprise ascorbic acid.

A further aspect of the invention relates to a method for the production of an artificial vitreous humor composition, preferably as described herein. The method comprises step (i), wherein stock solutions of glucose, creatinine, sodium lactate, glutathione and urea in water, a stock solution of hypoxanthine in formic acid:water of 2:1 ratio, and a stock solution of xanthine sodium in 1M NaOH are provided. The method further comprises step (ii) of mixing of the stock solutions of step (i) in a phosphate buffer with a pH value in the range from 7.0 to 7.7, particularly from 7.1 to 7.6, more particularly from 7.2 to 7.5, most particularly a pH value of 7.4, and pH adjustment to the pH value of the phosphate buffer. Preferably, mixing is performed with constant stirring of the mixture. In step (iii) hyaluronic acid is added to the mixture obtained in step (iii) and the mixture is stirred at 2 to 8° C. for at least 4 hours. Particularly, the mixture is stirred until the hyaluronic acid is completely dissolved. The method further comprises a step (iv), wherein collagen type-II is added, preferably with constant stirring, to the mixture obtained in step (iii). The mixture obtained in step (iv) is optionally sterile filtered.

The phosphate buffer may be selected from the group consisting of phosphate buffer saline (PBS), phosphate buffer saline inlcuding Tween (PBST), phosphate buffer saline inlcuding Tween and sodium azide (PBSTN) and phosphate buffer saline including sodium azide (PBSN). The phosphate buffer may be phosphate buffer saline (PBS). The phophate buffer saline may be in the range particularly from 0.001 to 0.2 M, more particularly from 0.003 to 0.05, most particularly from 0.005 to 0.02 M. The phophate buffer saline preferably has a pH value of 7.4. A preferred buffer according to the invention is 0.01 M PBS, pH 7.4 comprising 8 gm/L NaCl, 0.2 gm/L KCl, 1.44 gm/L $Na_2HPO_4$ and 0.24 gm/L $KH_2PO_4$.

The artificial vitreous humor composition may comprise at least one small molecular weight component. The small molecular weight component may be selected from the group consisting of creatinine, glucose, urea, xanthine, hypoxanthine, sodium lactate and glutathione. In a preferred embodiment, the aVH composition comprises 64.6 μM creatinine, 2.2 mM glucose, 7.6 mM urea, 580 μM xanthine, 309 μM hypoxanthine, 10.5 mM sodium lactate and 200 μM glutathione. Furthermore, the artificial vitreous humor composition may comprise 20 to 300 mg/L type II collagen and/or 0.03 to 0.9% w/v sodium hyaluronate. Collagen and/or sodium hyaluronate serve as matrix forming components in the artificial vitreous humor. In a preferred embodiment of the invention the artificial vitreous humor compositions comprises 40 mg/L type II collagen and/or 0.6% w/v sodium hyaluronate. In a preferred embodiment of the invention the artificial vitreous humor compositions comprises 40 mg/L type II collagen and 0.6% w/v sodium hyaluronate. The artificial vitreous humor composition may not comprise ascorbic acid.

A further aspect of the invention relates to a method for analyzing the behavior of a substance applied to an artificial vitreous humor composition, preferably as described herein. The method comprises step (i), wherein an artificial vitreous humor composition, preferably as described herein, is provided in an in-vitro environment. An in-vitro environment according to the invention may be a vial, preferably a glass vial or plastic vial, well, container, depression dish, ex-vivo intravitreal (ExVit) model as described in Patel et al., Evaluation of protein drug stability with vitreous humor in a novel ex-vivo intraocular model, European Journal of Pharmaceutics and Biopharmaceutics. 2017; 112:117-186 (which is incorporated herein by reference in its entirety), and any specially designed glass or plastic device. The method further comprises step (ii), wherein the substance to be analyzed is applied to the artificial vitreous humor. The substance may be administered to the artificial vitreous humor composition. Particularly, the substance may be injected to the artificial vitreous humor composition or diffused into the artificial vitreous humor composition or released from a long-acting sustained release delivery (DDS) system into the artificial vitreous humor composition. Furthermore, the method comprises step (iii) wherein at least one property of the applied substance is determined. As the property of the substance to be applied is known prior to the application to the vitreous humor, a comparison of the property of the substance before and after application to the artificial vitreous humor is feasible; e.g. in order to analyze the stability of the applied substance when present in the aVH, bioavailability, release from DDS system and degradation of the DDS system (Blanco et al., Protein encapsulation and release from poly(lactide-co-glycolide) microspheres: effect of the protein and polymer properties and of the co-encapsulation of surfactants, European journal of pharmaceutics and biopharmaceutics. 1998 May; 45(3): 285-94) within the aVH. The property of the substance may be determined immediately and/or in intervals in order to follow the change of the property over time.

The substance to be applied may be at least one of a macromolecule, a protein, e.g. an antibody, a peptide, an oligonucleotide, an aptamer, a drug formulation, an excipient, a small molecule, a drug delivery system (biodegradable and nonbiodegradable), or a combination thereof. However, the term substance is not to be understood as being limited to the aforementioned examples.

The substance to be applied may comprise molecules having a size in a range between 100 Da and 1800 kDa, particularly in a range between 1 kDa and 500 kDa, more particularly between 4 kDa and 200 kDa, most particularly between 10 kDa and 175 kDa.

The at least one property of the applied substance is selected from the group consisting of stability, bioavailability, release from DDS system and degradation of DDS system.

The applied substance may be left in the artificial vitreous humor composition for up to 360 days, particularly up to 180 days, more particularly up to 90 days, prior to step (iii). However, as mentioned earlier the property of the substance may be determined in intervals in order to follow the change of the property with time. Then, step (iii) may define the last determination in time of the at least one property. The artificial vitreous humor may be maintained at a constant temperature prior to step (iii), particularly at a temperature in the range from 32 to 38° C., more particularly from 35 to 37° C., most particularly from 36 to 37° C.

A further aspect of the invention relates to a method for analyzing the behavior of an artificial humor composition as described herein, wherein a substance is applied to the artificial humor composition. The method comprises step (i), wherein an artificial vitreous humor composition, preferably as described herein, is provided in an in-vitro environment. An in-vitro environment according to the invention may be a vial, preferably a glass vial or plastic vial, well, container, depression dish, ex-vivo intravitreal (ExVit) model as described in Patel et al., Evaluation of protein drug stability with vitreous humor in a novel ex-vivo intraocular model, European Journal of Pharmaceutics and Biopharmaceutics. 2017; 112:117-186 (which is incorporated herein by reference in its entirety), and any specially designed glass or plastic device. The method further comprises step (ii), wherein a substance is applied to the artificial vitreous humor. The substance may be administered to the artificial vitreous humor composition. Particularly, the substance may be injected to the artificial vitreous humor composition or diffused into the artificial vitreous humor composition or released from a long-acting sustained release delivery (DDS) system into the artificial vitreous humor composition. Furthermore, the method comprises step (iii) wherein at least one property of the artificial humor composition is determined. As the property of the artificial humor composition is known prior to the application of the substance, a comparison of the property of the the artificial humor composition before and after application of the substance is feasible; e.g. in order to analyze the stability and/or viscosity of the the artificial humor composition when the substance is present. Generally, the method allows an assessment of the tolerability of the artificial humor composition in view of the applied substance, particularly by determining the change of at least one of the group consisting of viscosity, turbidity, osmolality. The property of the the artificial humor composition may be determined immediately and/or in intervals in order to follow the change of the property over time. The substance to be applied may be at least one of a macromolecule, a protein, e.g. an antibody, a peptide, an oligonucleotide, an aptamer, a drug formulation, an excipient, a small molecule, a drug delivery system (biodegradable and non-biodegradable), or a combination thereof. However, the term substance is not to be understood as being limited to the aforementioned examples. The substance to be applied may comprise molecules having a size in a range between 100 Da and 1800 kDa, particularly in a range between 1 kDa and 500 kDa, more particularly between 4 kDa and 200 kDa, most particularly between 10 kDa and 175 kDa. The applied substance may be left in the artificial vitreous humor composition for up to 360 days, particularly up to 180 days, more particularly up to 90 days, prior to step (iii). However, as mentioned earlier the property of the the artificial humor composition may be determined in intervals in order to follow the change of the property with time. Then, step (iii) may define the last determination in time of the at least one property. The artificial vitreous humor may be maintained at a constant temperature prior to step (iii), particularly at a temperature in the range from 32 to 38° C., more particularly from 35 to 37° C., most particularly from 36 to 37° C.

A further aspect of the invention relates to a method for analyzing the behavior of a substance in a artificial humor as described herein and/or the behavior of an artificial humor composition as described herein.

A further aspect of the invention relates to an artificial vitreous humor composition as described herein produced by the method of production as described herein.

A further aspect of the invention relates to a kit of parts for the production of an artificial vitreous humor composition, particularly as described herein. The kit of parts comprises several components. Component (A) is a phosphate buffer, particularly phosphate buffer saline (PBS), more particularly 0.01 M phosphate buffer saline (PBS), having a pH value in the range from 7.0 to 7.7, particularly from 7.1 to 7.6, more particularly from 7.2 to 7.5. most particularly a pH value of 7.4. Component (B) comprises at least one selected from the group consisting of creatinine, glucose, urea, xanthine, hypoxanthine, sodium lactate, glutathione. Preferably, component (B) comprises a mixture of creatinine, glucose, urea, xanthine, hypoxanthine, sodium lactate, glutathione or component (B) is a selection of components referred to as (B1) creatinine, (B2) glucose, (B3) urea, (B4) xanthine, (B5) hypoxanthine, (B6) sodium lactate and (B7) glutathione. Component (C) comprises type II collagen and/or sodium hyaluronate. Preferably, component (C) is a selection of components referred to as (C1) type II collagen and (C2) sodium hyaluronate. Optional component (D) is instructions for use.

A further aspect of the invention relates to the use of an artificial vitreous humor composition as described herein in a method for analyzing the behavior of a substance in the artificial humor composition as described herein. A further aspect of the invention relates to the use of an artificial vitreous humor composition as described herein in a method for analyzing the behavior of the artificial vitreous humor composition, when a substance is applied to the artificial vitreous humor composition. A further aspect of the invention relates to the use of an artificial humor composition as described herein in a method for analyzing the behavior of a substance in the artificial composition as described herein and/or in a method for analyzing the behavior of the artificial humor composition, wherein a substance is applied to the artificial humor composition, as described herein.

A further aspect of the invention relates to the use of a phosphate buffer saline having a pH value in the range from 7.0 to 7.7, particularly from 7.1 to 7.6, more particularly from 7.2 to 7.5, most particularly a pH value of 7.4 for the production of an artificial vitreous humor composition as described herein.

BRIEF DESCRIPTION OF THE FIGURES

FIG. 6a represents the main peak. FIG. 6b represents the higher molecular weight species (HMWS, %) (Experiments were performed in triplicates and results are reported in mean±std. dev).

FIG. 7a represents the main peak. FIG. 7b represents the deglycosylated variants (area %).

FIG. 8a represents binding affinity to antigen-1. FIG. 8b represents the binding affinity to antigen-2 retrieved from stability samples following incubation in aVH (ExVit or vial model) and pVH.

DETAILED DESCRIPTION OF EMBODIMENTS OF THE INVENTION

I. Definitions

Figure 1:
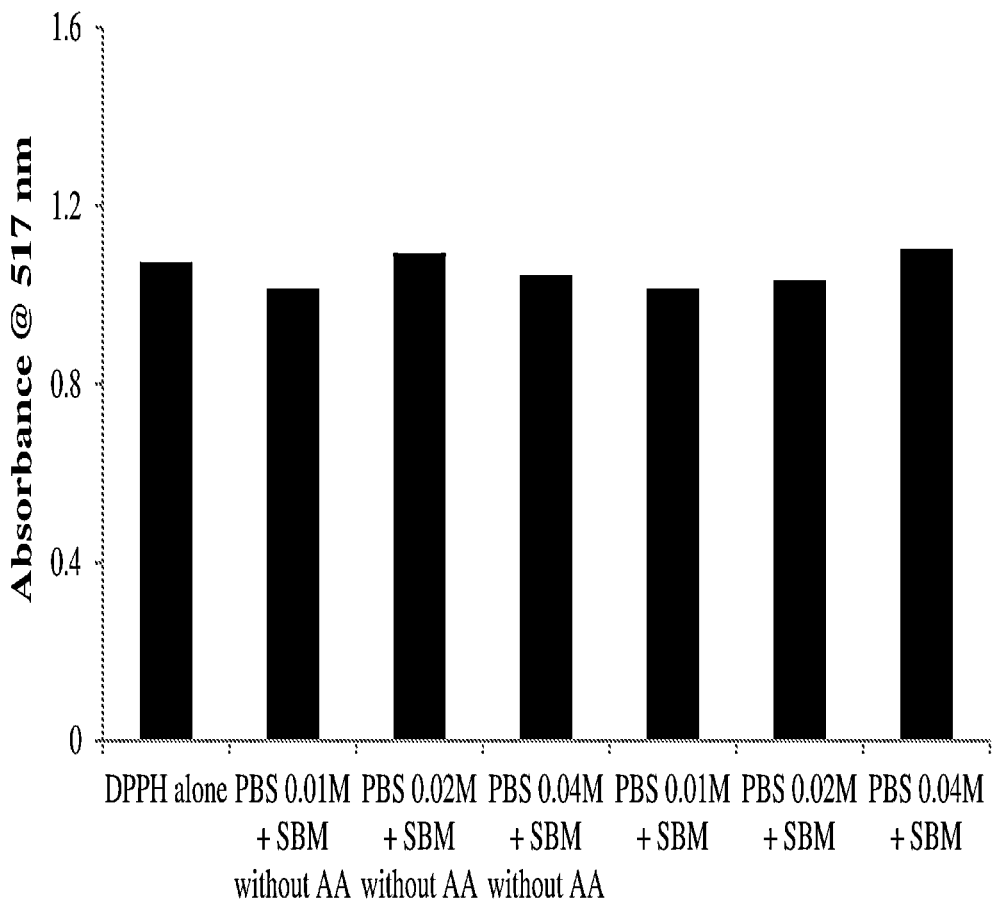
FIG. 1: Absorbance analysis correlating to the amount of reduced ascorbic acid in three different simulated buffer media (SBM) prepared at different buffer strength after 1 week of incubation at 37° C.

"Vitreous humor" as used in this application may be from natural or artificial sources. Natural vitreous humor may be from various animal species, for example porcine, bovine, canine, feline, from rabbits and non-human primates or may be human. Porcine vitreous humor is abbreviated pVH herein. Natural vitreous humor may for example be gained from eyes that have previously been removed.

Artificial vitreous humor preferably mimics human vitreous humor. Artificial vitreous humor may be prepared from various polymeric materials, also called large molecular weight (LMW) components or matrix forming components, for example natural polymers such as but not limited to hyaluronic acid, alginate, agar, chitosan, gelatin, xanthan gum, pectins, collagen, or for example synthetic polymers such as but not limited to pluronic gel, polyvinyl alcohol, polyphosphazenes, any dimeric, trimeric or multimeric gelling polymers composed of PEG, PCL, PLA, PGA, PLGA, poly acrylamide, polyacrylic acid, as well as combinations of these polymers at different concentrations. The amount of LMW components, particularly the hyaluronic acid, may be chosen to achieve a defined viscosity of the final aVH composition. Artificial vitreous humor may further comprise small molecular weight (SMW) components. These small molecular weight components may be selected from the group comprising nitrogenous organic acids, sugars, reducing agents, such as urea, purine bases or derivatives thereof, salts of lactic acid and antioxidants, such as glutathione.

Vitreous humor may also be a mixture of artificial and natural vitreous humor or their components in different combinations.

A "buffer solution" is a solution preferably having or being able to maintain the pH value of the system, for example between pH 5.5 and pH 8.5, preferably between about pH 7.0 and about pH 7.6, more preferably at pH 7.4. "Physiologically relevant buffer solution" is a solution preferably having or being able to maintain a pH value of the system between about pH 7.0 and about pH 7.6, more preferably at pH 7.2-7.4. Preferably, a buffer solution comprises salts. The buffer solution may for example be a phosphate buffered saline (PBS), a bicarbonate buffer, Ringer's bicarbonate buffer, Ringer's lactate buffer, simulated body fluids, other isotonic solutions, cell culture medias, and any other physiologically representative buffers.

PBS according to the invention may comprise 8 gm/L NaCl, 0.2 gm/L KCl, 1.44 gm/L $Na_2HPO_4$ and 0.24 gm/L $KH_2PO_4$. PBS preferably has a pH value of 7.4.

The term "behavior of a substance" relates to the change of a property of a substance when applied to the artificial vitreous humor or else to the artificial humor composition according to the invention. The change of property of a substance can be a) chemical or physical changes, b) change in its binding to a target, c) transformation from one polymorphic form to another polymorphic form, d) change of physical state, e.g. liquid to gel. A substance can be a therapeutic agent or two or more therapeutic agents, excipient, formulation (simple or sustained release) or placebo (simple or placebo of sustained release formulation).The composition of artificial VH (aVH) allows simulating in vivo physiological conditions of natural VH. For example, with injection of a drug formulation into vitreous humor, the formulation's stability and release from DDS may be simulated, for human but also for animal eyes. For example, different diffusion and precipitation behavior may be tested for, for example, different proteins in different eye conditions (corresponding to more or less degenerated eyes, by age or by disease) for posterior eye tissue. These conditions can be simulated and tested with the aVH and the method for analyzing the behavior of a substance according to the invention by varying the properties, e.g. composition and/or density and/or viscosity, of the aVH. In addition, more realistic test results may be achieved, especially on stability and release of a substance from DDS, for example a protein or a drug formulation, by taking into account the physical and chemical environment present at the injection location. Thus, artificial vitreous humor and the method according to the invention allow to more realistically simulate the geometry of a natural environment, preferably of an eye environment.

The term "behavior of an artificial humor composition" relates to the change of a property of the artificial humor composition, when a substance is applied to the artificial vitreous humor according to the invention. The change of property of the artificial humor composition can particularly be chemical or physical changes, and/or change of physical state, e.g. gel to liquid.

II. Examples

Materials

Porcine eyes were acquired from a local slaughter-house located near Zurich, Switzerland. Custom made side-by-side diffusion chambers were purchased from SES GmbH-Analytical Systems (Bechenheim, Germany) A diffusion controlling membrane, with molecular weight cut-off (MWCO) of 50 kDa (cat #131384), was procured from Spectrum lab (California, USA). Collagen (type-II) (cat #804001-sol) and sodium hyaluronate (cat #HA15M) were purchased from mdbioproducts and Lifecore Biomedical, respectively. L-ascorbic acid (cat #A5960), xanthine sodium salt (cat #X3627), hypoxanthine (cat #H9636), creatinine (cat #C4255), urea (cat #51457), glucose (cat #G8270), L-glutathione (cat #G4251) and sodium lactate (cat #71718) were procured from Sigma Aldrich, USA. Bispecific monoclonal antibody (mAb) was manufactured in a CHO cell line and provided by F.Hoffmann-La Roche AG, Basel. The mAb is a full length humanized mAb based on the IgG-1 format with an approximate molecular weight of 150 kDa. mAb was formulated in histidine buffer (20 mM, pH 6.0) containing sugar and surfactant to provide tonicity and stability, respectively. The small molecule with a MW<600 Dalton and Log P of 3.24 was provided by F. Hoffmann-La Roche AG, Basel. PLGA polymers were procured from Evonik, Parsippany, USA (RG756S PL(DL)GA 75:25 and RG753H PL(DL)GA 75:25). In all the experiments related to the ExVit model, phosphate buffer saline (0.01 M PBS, pH 7.4) was used in the buffer-compartment. All other reagents utilized in these studies were of analytical grade.

Example 1

Development of a Simulated Buffer Medium (SBM)

Natural VH is a liquid tissue mainly composed of water with small amounts of organic and inorganic components including matrix forming polymers. The composition of VH is reported in literature. In order to prepare artificial VH (aVH), firstly, it was important to identify a base buffer system which can support the physicochemical stability of aVH. Secondly, it was important to prepare a simulated buffer medium (SBM) containing all the small molecular weight components of the natural VH in a defined concentration as reported in literature. At last, SBM was prepared in the presence of matrix forming polymers i.e., hyaluronic acid and collagen, inherent components of natural VH. Stability of the aVH was then evaluated by storing it at 37° C. for 3 months.

In order to identify the right buffer system, two biologically relevant buffer systems supporting physiological pH such as Kerbs Ringer bicarbonate buffer and phosphate buffer saline (PBS) were investigated. The compositions of buffer systems are given in Table 1 and 2.

TABLE 1

Composition of bicarbonate Buffer (Modified
Krebs ringer buffer, pH 7.4)

| Components | Concentration |
|---|---|
| $MgCl_2$ | 0.0538 gm/L |
| KCl | 0.876 gm/L |
| NaCl | 9.29 gm/L |
| $Na_2HPO_4$ | 0.1 gm/L |
| $NaH_2PO_4$ | 0.18 gm/L |
| $NaHCO_3$ | 1.26 gm/L |
| $CaCl_2$ | 0.232 gm/L |

TABLE 1-continued

Composition of bicarbonate Buffer (Modified
Krebs ringer buffer, pH 7.4)

| Components | Concentration |
|---|---|

TABLE 2

Composition of phosphate buffer saline (PBS, 0.01M, pH 7.4)

| Components | Concentration |
|---|---|
| NaCl | 8 gm/L |
| KCl | 0.2 gm/L |
| Na2HPO4 | 1.44 gm/L |
| KH2PO4 | 0.24 gm/L |

The following small molecular weight (SMW) components, hypoxanthine (309 μM), creatinine (64.6 μM), xanthine (580 μM), ascorbic acid (350 μg/mL), glucose (2.2 mM), urea (7.6 mM), sodium lactate (10.5 mM) and glutathione (200 μM) are reported in the literature as key components of the VH. Hence, they were utilized for the preparation of SBM. As described in the Table 3 and Table 4, various compositions of SBM (composition 1-17) were prepared with and without specific SMW components dissolved in either bicarbonate or PBS based buffering system.

TABLE 3

Impact of small MW components on the storage stability of simulated buffer
medium (SBM) at 37° C. with Kerbs Ringer bicarobonate based buffering system

| # | Hypoxanthine (309 μM) | Creatinine (64.6 μM) | Xanthine (580 μM) | Ascorbic acid (350 μg/mL) | Glucose (2.2 mM) | Urea (7.6 mM) | Sodium lactate (10.5 mM) | Glutathione (200 μM) | Clarity 3 days | Clarity 7 days | pH Initial | pH 7 days |
|---|---|---|---|---|---|---|---|---|---|---|---|---|
| 1 | + | + | + | + | + | + | + | + | Clear | Turbid | Physiological | Acidic |
| 2 | | + | + | + | + | + | + | + | Turbid | Turbid | Physiological | Acidic |
| 3 | + | | + | + | + | + | + | + | Clear | Turbid | Physiological | Acidic |
| 4 | + | + | | + | + | + | + | + | Clear | Turbid | Physiological | Acidic |
| 5 | + | + | + | | + | + | + | + | Clear | Turbid | Physiological | Acidic |
| 6 | + | + | + | + | | + | + | + | Clear | Turbid | Physiological | Acidic |
| 7 | + | + | + | + | + | | + | + | Clear | Turbid | Physiological | Acidic |
| 8 | + | + | + | + | + | + | | + | Clear | Turbid | Physiological | Acidic |
| 9 | + | + | + | + | + | + | + | | Clear | Turbid | Physiological | Acidic |

TABLE 4

Impact of SMW components on the storage stability of simulated buffer medium
(SBM) at 37° C. with Phosphate Buffer Saline (PBS, pH 7.4, 0.01M) based buffering system

| # | Hypoxanthine (309 μM) | Creatinine (64.6 μM) | Xanthine (580 μM) | Ascorbic acid (350 μg/mL) | Glucose (2.2 mM) | Urea (7.6 mM) | Sodium lactate (10.5 mM) | Glutathione (200 μM) | Clarity 3 days | Clarity 7 days | pH Initial | pH 7 days |
|---|---|---|---|---|---|---|---|---|---|---|---|---|
| 10 | + | + | + | + | + | + | + | + | Clear | Clear | Physiological | Acidic |
| 11 | | + | + | + | + | + | + | + | Clear | Clear | Physiological | Acidic |
| 12 | + | | + | + | + | + | + | + | Clear | Clear | Physiological | Acidic |
| 13 | + | + | | + | + | + | + | + | Clear | Clear | Physiological | Acidic |
| 14 | + | + | + | + | | + | + | + | Clear | Clear | Physiological | Acidic |
| 15 | + | + | + | + | | + | + | + | Clear | Clear | Physiological | Acidic |
| 16 | + | + | + | + | + | | + | + | Clear | Clear | Physiological | Acidic |
| 17 | + | + | + | + | + | + | | + | Clear | Clear | Physiological | Acidic |

These SBMs were sterile filtered with 0.22µ filter under laminar air flow. SBMs were then investigated for storage stability by incubating at 37° C. for 7 days. Buffer compatibility was evaluated by measuring pH and clarity. For pH estimation, samples (100 µL) were aseptically transferred in eppendorf tubes and analyzed by calibrated pH meter (827 pH Lab, Metrohm, Switzerland). Clarity of the SBMs was observed visually and the samples were classified as clear or turbid.

In Table 3, all the studied compositions (1-9) containing Kerbs Ringer bicarbonate buffer showed turbidity and instability with respect to pH after one week of incubation. The instability with respect to pH relates to an acidic shift. This may be due to the weak buffering capacity of bicarbonate based buffer system and/or due to the incompatibility of buffer system with small molecular weight components. In summary, it would not be possible to develop SBM with Kerbs Ringer bicarbonate buffer mainly due to turbidity and pH shift.

On the other hand, PBS based SBM compositions 10-17 remained clear after 7 days of incubation at 37° C. (Table 4). However, all of these compositions also showed acidic pH shift after 7 days.

Example 2

Impact of Higher Buffer Strength, Sodium Lactate, Hypoxanthine and Ascorbic Acid on the Stability of SBMs In order to find stable composition, SBM with or without sodium lactate, hypoxanthine and ascorbic acid, and SBM with higher buffer strength were investigated. The SBMs were prepared as reported in Table 5.

cient to maintain the pH. Also, absence of sodium lactate and hypoxanthine or both also could not prevent the acidic pH shift (compositions 21-27). Only SBM compositions 28-30, without ascorbic acid exhibited stable pH after 7 days. Furthermore as shown in the DPPH of FIG. 1, SBMs with or without Ascorbic acid exhibited similar levels of absorbance at 517 nm suggesting absence of reduced form of ascorbic acid after 7 days of incubation at 37° C. Ascorbic acid might be oxidized in less than 7 days resulting in the pH shift to the acidic side. Hence, ascorbic acid was not included in the final SBM composition.

Example 3

Long Term Stability of SBM

Once the composition 28 of SBMs was found stable for 7 days without change in pH or clarity, it was further characterized for long-term storage stability at 37° C. Briefly, composition 28 was prepared and aseptically filtered under LAF. The sterile SBM was then transferred aseptically in 6 mL sterile glass vials. The glass vials were sealed and incubated at 37° C. for 3 months. The samples were collected at various time points such as, initial, week-1, week-2, week-5, week-8 and week-12, and analyzed for pH, clarity, density, viscosity and osmolality. For pH estimation, samples (100 µL) were aseptically transferred in eppendorf tubes and analyzed by calibrated pH meter (827 pH Lab, Metrohm, Switzerland). Clarity of the SBMs was observed visually and the samples were classified as clear or turbid. Density of the SBM was estimated at 20° C. using DMA 38

TABLE 5

Impact of buffer strength and presence/absence of sodium lactate, hypoxanthine, and ascorbic acid on the storage stability of simulated buffer medium (SBM) at 37° C.

| # | PBS (pH 7.4) | Hypoxanthine (309 µM) | Creatinine (64.6 µM) | Xanthine (580 µM) | Ascorbic acid (350 µg/mL) | Glucose (2.2 mM) | Urea (7.6 mM) | Sodium lactate (10.5 mM) | Glutathione (200 µM) | pH Initial | pH 7 days |
|---|---|---|---|---|---|---|---|---|---|---|---|
| 10 | 0.01M | + | + | + | + | + | + | + | + | Physiological | Acidic |
| 18 | 0.015M | + | + | + | + | + | + | + | + | Physiological | Acidic |
| 19 | 0.02M | + | + | + | + | + | + | + | + | Physiological | Acidic |
| 20 | 0.04M | + | + | + | + | + | + | + | + | Physiological | Acidic |
| 21 | 0.015M | | + | + | + | + | + | + | + | Physiological | Acidic |
| 22 | 0.02M | | + | + | + | + | + | + | + | Physiological | Acidic |
| 23 | 0.015M | + | + | + | + | + | + | | + | Physiological | Acidic |
| 24 | 0.02M | + | + | + | + | + | + | | + | Physiological | Acidic |
| 25 | 0.01M | | + | + | + | + | + | | + | Physiological | Acidic |
| 26 | 0.015M | | + | + | + | + | + | | + | Physiological | Acidic |
| 27 | 0.02M | | + | + | + | + | + | | + | Physiological | Acidic |
| 28 | 0.01M | + | + | + | | + | + | + | + | Physiological | Stable |
| 29 | 0.02M | + | + | + | | + | + | + | + | Physiological | Stable |
| 30 | 0.04M | + | + | + | | + | + | + | + | Physiological | Stable |

SBMs were sterile filtered and incubated at 37° C. for one week and analyzed for pH and clarity. Samples were collected and analysis was performed as described above. Also, the amount of reduced ascorbic acid was analyzed in the samples using 1,1-diphenyl-2-picrylhydrazyl (α,α-diphenyl-β-picrylhydrazyl (DPPH) assay. Briefly, 100 µL of ascorbic acid standard or test samples were incubated in presence of 1900 µL of DPPH solution at 37° C. for 30 min in dark. Samples were then analyzed for change in optical density (OD) at 517 nm against methanol as blank. The presence of ascorbic acid turns color of solution from violet to brownish-pale yellow.

The pH results depicted in Table 5 clearly show that higher buffer strength (compositions 18-20) was not suffi- (Anton Paar) densiometer. Osmolality of the samples were estimated with a calibrated osmometer (Osmomat 030 3P Cryoscopic Osmometer) in the range of 0-0.5 Osmol/kg according to European Pharmacopoeia, Osmolality, Section 2.2.35, European Directorate for the Quality of Medicine, Strasbourg, France, 2017, pp. 59. Following calibration, 50 µL of the samples were placed in the osmometer and the osmolality was evaluated. Viscosity was analyzed using SV-1A vibro viscometer. Briefly, 2 mL of sample was transferred in the sample holder and vibrating plates were inserted in the samples making sure that plates do not touch at the bottom or side walls of sample holder. Viscosity was measured and reported in mPa·S.

TABLE 6

Long-term storage stability of simulated buffer medium (SBM) at 37° C.

| | Initial | Week 1 | Week 2 | Week 5 | Week 8 | Week 12 |
|---|---|---|---|---|---|---|
| Density | 1.006 | — | — | 1.0057 | 1.0057 | 1.0056 |
| Osmolality (Osmol/kg) | 0.297 | 0.295 | 0.295 | 0.298 | 0.297 | 0.299 |
| pH | 7.27 | 7.31 | 7.31 | 7.32 | 7.29 | 7.31 |
| Viscosity (mPa · s) | 1.00 | 1.02 | 0.99 | 1.03 | 1.01 | 1.02 |
| Clarity | Clear | Clear | Clear | Clear | Clear | Clear |

The data depicted in Table 6 show that SBM remained stable during the study period of 3 months. No change in pH, clarity, density, osmolality or viscosity were observed during the investigation. Hence, the SBM composition without ascorbic acid at lower PBS strength (composition-28) was selected as suitable SBM for the development of aVH.

Example 4

Viscosity Assessment of Natural Vitreous Humor

Viscosity of the study/release medium (in this case aVH) would have significant impact on the rate of release of therapeutic agents from the DDS systems. Therefore, viscosity of the aVH has to be similar to the natural VH. As mentioned earlier, VH is the liquid tissue which behaves like a gel under pressure when it is in the eye. As soon as VH is isolated from the eye, it liquefies mainly due to the disorientation of collagen fibers. Rheological properties of VH are highly influenced by collagen fibrillary concentration and orientation. Usually collagen fibrils are arranged in a specific order initiating from vitreous base to the back of the eye (Le Goff et al., Adult vitreous structure and postnatal changes, Eye. 2008 October; 22(10): 1214-22). Hence, it is very important to estimate the viscosity of the VH in-situ without damaging structure of VH matrix. Due to the complexity in analytical procedure, no specific information about the actual in-vivo viscosity of the natural VH is available. Here, we have estimated the viscosity of natural VH in-situ using a vibro viscometer, so this information can be used to prepare aVH with appropriate viscosity.

Freshly isolated porcine eyes were procured from a slaughter house without any further processing such as heat treatment. Throughout the transportation, the eyes were stored in isotonic solution kept in an ice bath. Prior to the viscosity measurement, the eyes were stored at 37° C. for 2 hours. After the incubation, eyes were cut open from sclera (1×1 cm) to access VH. Vibration plates were inserted in the eyes making sure that the plates do not touch at the bottom or side walls. Also, to understand the impact of orientation of collagen fiber on the overall viscosity, the viscosity was measured by placing vibrating plates perpendicular or parallel to collagen fibers.

Figure 2:
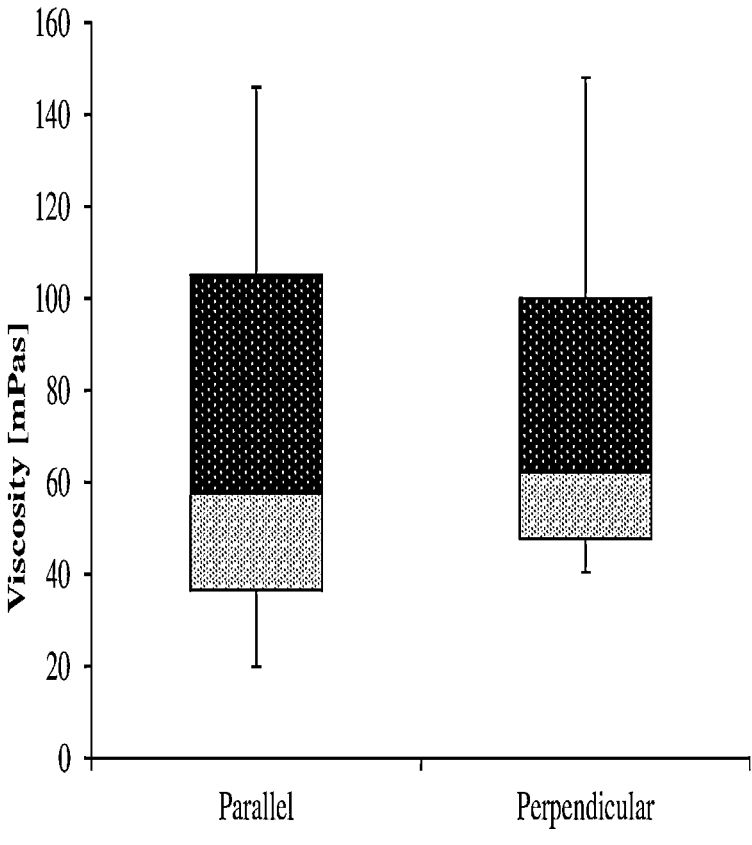
FIG. 2: Determination of the viscosity of isolated porcine vitreous humor.

As described in FIG. 2, natural, here porcine, VH exhibited 71±43 mPa·S of viscosity when the plates were placed parallel to the collagen fibers. Interestingly, viscosity was not significantly different when the plates were located perpendicularly to the collagen fibers (78±42 mPa·S). Because hyaluronic acid along with collagen (in a defined orientation) is mainly responsible for the viscosity of the natural VH, the same components were considered as a viscosity enhancer in the aVH. According to concentration vs viscosity results of hyaluronic acid solution (Table 7), 0.6% w/v of HA was used to prepare aVH. Here, it is important to note that similar viscosity of the aVH can be achieved using different molecular weight hyaluronic acids at different concentrations.

TABLE 7

Viscosity of aqueous hyaluronic acid solution with an average molecular weight of 1.01 to 1.8 MDa at different concentrations

| hyaluronic acid (Concentration % w/v) | Viscosity (mPa · s) |
|---|---|
| 0 | 0.98 ± 0 |
| 0.03 | 1.78 ± 0.02 |
| 0.1 | 7.47 ± 0.01 |
| 0.2 | 18.3 ± 0.13 |
| 0.4 | 42.24 ± 0.22 |
| 0.6 | 72.88 ± 2.88 |
| 0.9 | 139.37 ± 2.80 |

Example 5

Preparation of a Preferred Artificial VH Using SBM

Once the long-term stability of SBM was ensured, it was utilized to prepare aVH. Briefly, optimized SBM was prepared as described in previous section and then a defined amount of hyaluronic acid (HA) was added to prepare 0.6% of HA-SBM solution. HA was solubilized in SBM by stirring overnight at 2-8° C. The following day, collagen type-II was added in the HA-SBM solution to prepare the final collagen concentration of 40 mg/L. The resulting aVH was aseptically filtered through 0.22μ filter. The aVH was stored at 2-8° C. until further use. The final composition of a preferred aVH is reported in Table 8.

TABLE 8

Composition of a preferred artificial vitreous humor

| | | Components | Concentration |
|---|---|---|---|
| Optimized Simulated Buffer Medium (SBM) | PBS, pH 7.4 | NaCl | 6.4 gm/L |
| | | KCl | 0.16 gm/L |
| | | $Na_2HPO_4 \cdot 2H_2O$ | 1.80 mg/L |
| | | $KH_2PO_4$ | 0.24 gm/L |
| | Small MW components | Creatinine | 64.6 μM |
| | | Glucose | 2.2 mM |
| | | Urea | 7.6 mM |
| | | Xanthine | 580 μM |
| | | Hypoxanthine | 309 μM |
| | | Sodium lactate | 10.5 mM |
| | | Glutathione | 200 μM |
| Matrix forming components | | Collagen (type II) | 40 mg/L |
| | | Sodium Hyaluronate | 0.6% w/v |

Example 6

Storage Stability of Artificial Vitreous Humor (aVH)

aVH was investigated for the storage stability at 37° C. For this study, 3 mL of aVH was aseptically transferred in 6 mL sterile glass (type-I) vial and incubated at 37° C. for 3 months. Samples were collected at pre-defined time intervals i.e., initial, week-1, week-2, week-5, week-8 and week-12, and analyzed for pH, osmolality, density and viscosity. The analysis was performed with the protocols described herein.

TABLE 9

| | Initial | Week 1 | Week 2 | Week 5 | Week 8 | Week 12 |
|---|---|---|---|---|---|---|
| Density | 1.0073 | — | — | 1.0073 | 1.0074 | 1.0074 |
| Osmolality (Osmol/kg) | 0.307 | 0.303 | 0.300 | 0.307 | 0.306 | 0.308 |
| pH | 7.15 | 7.19 | 7.18 | 7.19 | 7.19 | 7.19 |
| Viscosity (mPa · s) | 71.5 | 72.7 | 74.9 | 73.4 | 72.6 | 63-66 |

Long-term storage stability of artificial VH at 37° C.

As described in Table 9, all the physicochemical parameters remained stable throughout the study period. Only a minor change in the viscosity at 3 month time point was observed which may be due to the partial degradation of the HA polymer. Hence, in a next step aVH was compared with natural VH for the evaluation of protein stability.

Once, the aVH was found stable for 3 months at 37° C., 50 µl of 120 mg/ml bispecific monoclonal antibody (mAb) with a molecular weight of approximately 150 kDa was injected in the aVH and natural VH, and investigated for its stability. It was hypothesized that if the stability of mAb in natural VH and aVH found comparable, it can be confirmed that aVH has the potential to substitute natural VH for in-vitro/ex-vivo stability and/or release (from DDS formulations) investigations.

Example 7

Stability of mAb in the aVH and Natural VH (Experimental Setup)

In Patel et al., (Evaluation of protein drug stability with vitreous humor in a novel ex-vivo intraocular model. European Journal of Pharmaceutics and Biopharmaceutics. 2015; 95(Pt B):407-17) and Patel et al. (Evaluation of protein drug stability with vitreous humor in a novel ex-vivo intraocular model. European Journal of Pharmaceutics and Biopharmaceutics. 2017; 112:117-186) it was reported that as soon as the VH is isolated from the eye, the pH of the VH increases rapidly (to ca. pH 8.5). The rationale for this alkaline pH shift is not well understood, but the literature points towards the speedy alterations in the microenvironment of the VH upon isolation and/or the accumulation of degradation products of the VH. The elevated pH value (ca. pH 8.5) and concentrated degradants in the isolated VH can have a detrimental impact on the protein stability and can stimulate degradation of mAb which does not occur in in-vivo situation and make this study prone to artefacts. Presently, only one reliable tool developed is available to study the stability of protein drugs or drug delivery systems in the isolated pVH. The aforementioned ExVit model has successfully solved the problems with alkaline pH shift and generation of VH degradation products. In order to establish aVH as a stability prediction tool, it is very important to perform comparative study between aVH (in ExVit and vials) and isolated natural VH (in ExVit). Hence, three test groups were studied namely, 1) protein incubated in the aVH using the ExVit model, 2) protein incubated in isolated porcine VH (pVH) using the ExVit model, and 3) protein incubated in the aVH in a close vial model.

Isolation of the Porcine Vitreous Humor (pVH)

Porcine eyes were opened with the incision placed near the conjunctiva using a dissecting knife and the clear VH was collected with the disposable syringe without a needle. The VH was then sterile-filtered through a 0.22 µm filter to ensure removal of any microbial contamination and cellular debris. The VH was stored (in small aliquots) below −70° C.

to avoid possible metabolic activity and degradation or change in VH. Throughout the process of VH isolation, eye balls were kept in an ice-bath. All the experiments were performed according to the Association of Research in Vision and Ophthalmology (ARVO) statement for the use of animals in ophthalmic and vision research.

Experimental Set-Up

Figures 3A, 3B:
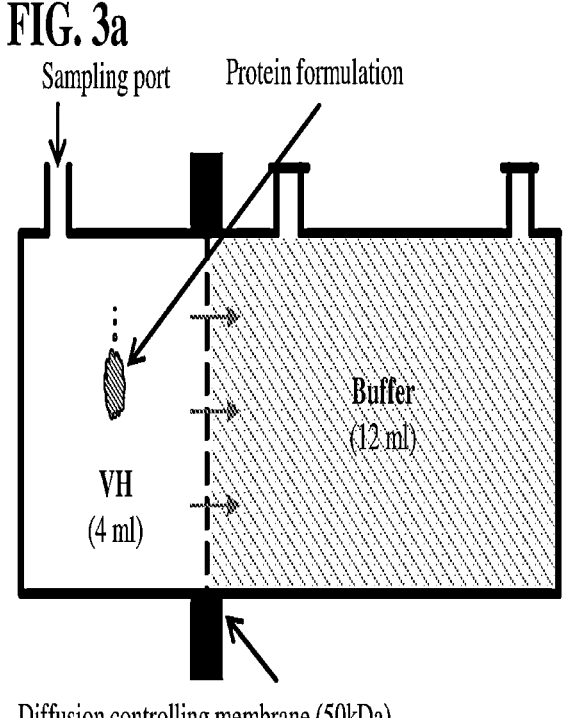
FIGS. 3a and 3b: Pictorial representations of the ExVit model utilized to compare protein stability in the natural VH vs artificial VH (FIG. 3a) and of vial based model used to investigate protein stability in the artificial VH (FIG. 3b).

The ExVit is a two compartment model, VH-compartment and buffer-compartment. As demonstrated in FIG. 3a, two compartments were separated by a diffusion controlling membrane with MWCO of 50 kDa. The buffer-compartment was always filled with sterile PBS (0.01 M, pH 7.4) whereas the VH-compartment was filled with the sterile pVH or sterile aVH. The devices were sealed with a sterile Teflon cap and incubated overnight at 37° C. (MaxQ-4000 incubator, Thermo Scientific). Following incubation, PBS from the buffer-compartment was replaced with fresh sterile PBS (pre-incubated at 37° C.). Simultaneously, 50 µL (120 mg/mL) of mAb was injected in the VH-compartment. Devices were sealed and incubated at 37° C. for the defined time intervals i.e., initial, week-2, week-4 and week-8. The VH-compartment containing pVH or aVH, without mAb, were considered as negative controls. Also, to investigate the effect of pH, temperature, and PBS on the stability of the mAb, the VH-compartment, filled with PBS, containing 50 µL of mAb was used as control. At defined time intervals, samples were aseptically transferred from VH-compartments in sterile glass vials. The performance of the model was evaluated by estimating the pH, osmolality and total protein concentration of samples. Samples were further evaluated to investigate physical stability and binding affinity of mAb.

Experimental Setup of aVH in Vials 2 mL of sterile filtered aVH was aseptically transferred in the sterile 6 mL glass vials (FIG. 3b). 25 µL of the 120 mg/mL of mAb formulation was injected in the test samples where as aVH without mAb was considered as control. Vials were incubated at 37° C. and samples were collected at defined time intervals i.e., initial, week-2, week-4 and week-8. Samples were analyzed by various analytical techniques to evaluate stability of mAb.

TABLE 10

Study design to investigate mAb stability in natural VH and artificial VH in two different model i.e., ExVit and vial.

| | ExVit Model | | |
|---|---|---|---|
| | VH-compartment | Buffer-compartment | Vial |
| Test-A | aVH + mAb | PBS | — |
| Test-B | pVH + mAb | PBS | — |
| Test-C | — | — | aVH + mAb |
| Control-A | PBS + mAb | PBS | — |

TABLE 10-continued

Study design to investigate mAb stability in natural VH and artificial
VH in two different model i.e., ExVit and vial.

| | ExVit Model | | |
| | VH-compartment | Buffer-compartment | Vial |
| Control-B | aVH | PBS | — |
| Control-C | pVH | PBS | — |
| Control-D | — | — | aVH |

Example 8

Stability of mAb in the aVH and Natural VH (Evaluation of Model Performance)

It was important to confirm that aVH can be investigated under ExVit and Vial model in the presence of mAb. In order to confirm that Test groups A, B & C and Control groups A, B, C and D (according to Table 10) were investigated for changes in pH, osmolality and clarity following long term incubation at 37° C. The pH was investigated at each time interval. Briefly, 100 μL of the samples were collected from the ExVit and vial model, from the controls (pVH alone, aVH alone, and buffer+mAb) and test articles (pVH+mAb, aVH+mAb). The pH and osmolality were analyzed as described earlier. The pH and osmolality results were plotted for the time interval vs pH unit or Osmol/kg, respectively.

Figures 4A, 4B:
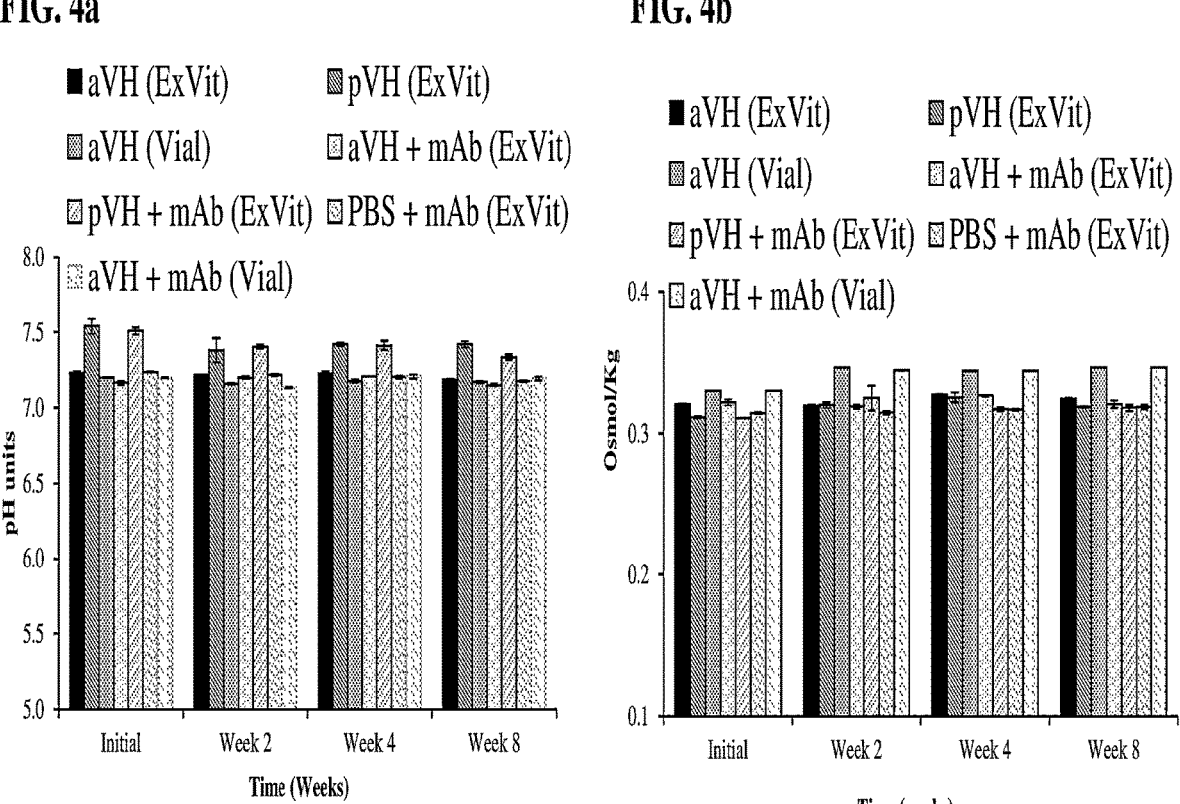
FIGS. 4a and 4b: Analysis of pH (FIG. 4a) and osmolality (FIG. 4b) of the PBS and vitreous humor (aVH and pVH) in ExVit or vial model with or without a monoclonal antibody (mAb) after incubation at 37° C. (Experiments were performed in triplicates and results are reported in mean±std. dev).

In-vivo, the VH is always buffered to physiological pH. Therefore, in order to mimic the long-term stability of mAb, it is very important to maintain the pH of the aVH or natural VH to physiological value. It can be clearly depicted from the data shown in FIG. 4a, that the pH value of all the test and control samples (ExVit or Vial model) following addition of a mAb formulation remained stable throughout the study period of 2 months. Furthermore, during the entire study, osmolality of the aVH and pVH were maintained between 0.31 and 0.33 Osmol/kg (FIG. 4b). It indicates that the mAb formulation was always homogeneously distributed within the aVH/pVH without altering their osmolality. In this study, aVH was found stable in the ExVit model as well as in the vial and hence protein stability investigated in the aVH can be compared with isolated pVH.

Example 9

Evaluation of Physical Stability of mAb in the aVH and Natural VH

Figure 5:
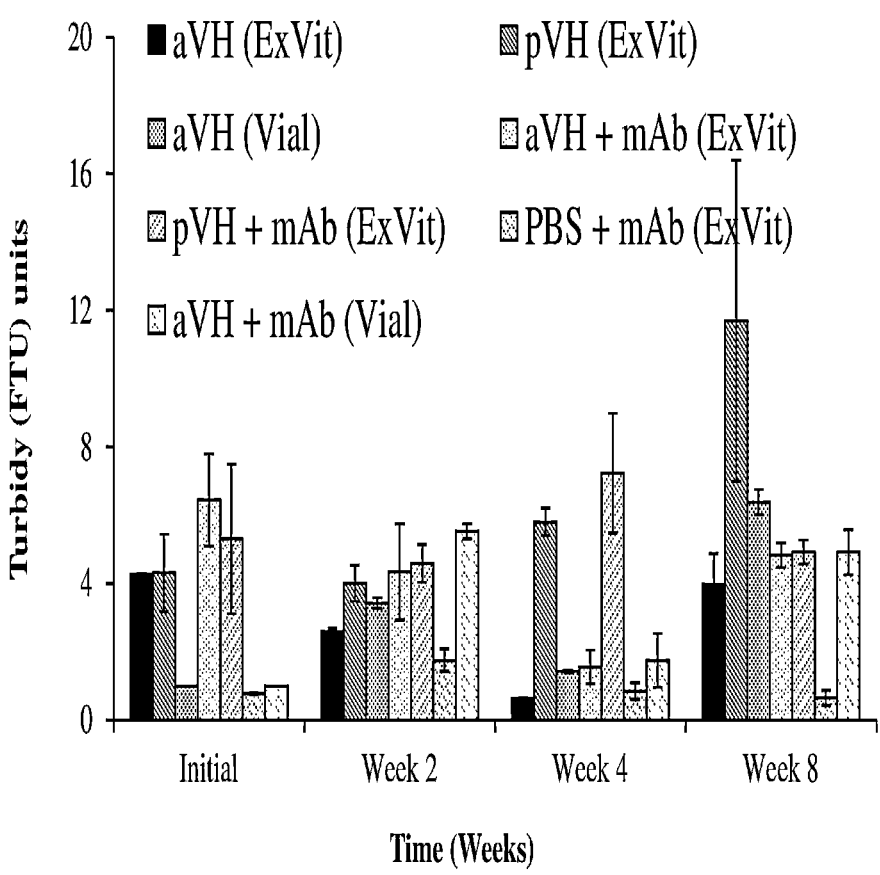
FIG. 5: Analysis of turbidity of the PBS and vitreous humor (aVH and pVH) in ExVit or vial model with or without mAb after incubation at 37° C. (Experiments were performed in triplicates and results are reported in mean±std. dev).

Samples were evaluated for the physical stability of mAb by various analytical techniques e.g., microscopy, turbidimetry, size exclusion chromatography (SEC), and capillary electrophoresis sodium dodecyl sulfate-non gel sieving (CE-SDS-NGS) as indicated in the following.
Microscopic Evaluation of Insoluble Particles Proteins are generally very sensitive towards the physical, chemical and environmental stress which can easily generate soluble and insoluble particles (large aggregates). To evaluate insoluble particles, at each time intervals 2 mL of the sample was transferred aseptically in sterile FTU tubes. The samples were assessed microscopically (Keyence VHX-600 digital microscope) for the presence of visible particles.
Turbidimetry Physical stability of protein could also be estimated by the turbidimetric analysis. Control and test samples at the selected time points were estimated for turbidity using 2100AN Turbidimeter (HACH). Instrument was calibrated between 0.1 and 150 NTU. To evaluate turbidity, at each time intervals 2 mL of sample was aseptically transferred in the sterile FTU tubes. The results were plotted for FTU unit vs time (FIG. 5).
Size Exclusion Chromatography (SEC)

The level of fragments and soluble aggregates of mAb were assessed using size-exclusion chromatography (SEC) coupled with a UV-visible detector. The SEC method was developed in-house for the estimation of mAb. Briefly, 50 μL of samples (controls and test specimens) were injected into the separation column procured from Tosch Bioscience (TSK gel, G3000SWXL, 7.8-300 mm, 5μ). The separation of aggregates and fragments were carried out at a flow rate of 0.5 mL/min using 0.2 M phosphate buffer (pH 7.0) as a mobile phase. UV-visible detection was performed at 280 nm with a Waters-2489 detector (Water Corp. MA, USA). Analysis was executed on a Waters 2695 HPLC (Waters Corp. MA, USA) and the data was processed utilizing Empower-2 software.
Capillary Electrophoresis Sodium Dodecyl Sulfate-Non Gel Sieving (CE-SDS-NGS)

Levels of soluble aggregates and fragments in the stability samples were further confirmed by the CE-SDS-NGS. CE-SDS-NGS analysis was performed under non-reducing condition with the Beckman Coulter Capillary Electrophoresis System (Proteome Lab PA800). The capillary was rinsed at 70 psi with 0.1 mM NaOH (for 5 min), 0.1 mM HCl (for 1 mM) and deionized water (for 1 min). The SDS MW gel buffer was loaded in the capillary at 50 psi. Non-reduced samples were then injected electrokinetically at 10 kV and analysis was carried out at 15 kV. The data was processed using 32-Karat software. The area of the main peak, aggregates, fragments, light-chain and heavy-chain were calculated, and the results were plotted as peak area (%) vs time.

Formation of particles and insoluble aggregates in test and control samples were assessed by observing the presence of visible particles using microscopic analysis (Microscopic evaluation and turbidity). The results exhibited no visible particles in any of the test or control groups after 2 months of incubation at 37° C. Also, no immediate precipitation or particle formation was observed when 50 μL of the mAb formulation was injected into the test or controls. The results were further confirmed by the turbidimetric analysis (FIG. 5), where turbidity readings for test groups remained below 10 FTU and they were also comparable with the controls. It suggests that no visible or sub-visible aggregates were generated during the incubation of mAb in the aVH.

Figures 6A, 6B:
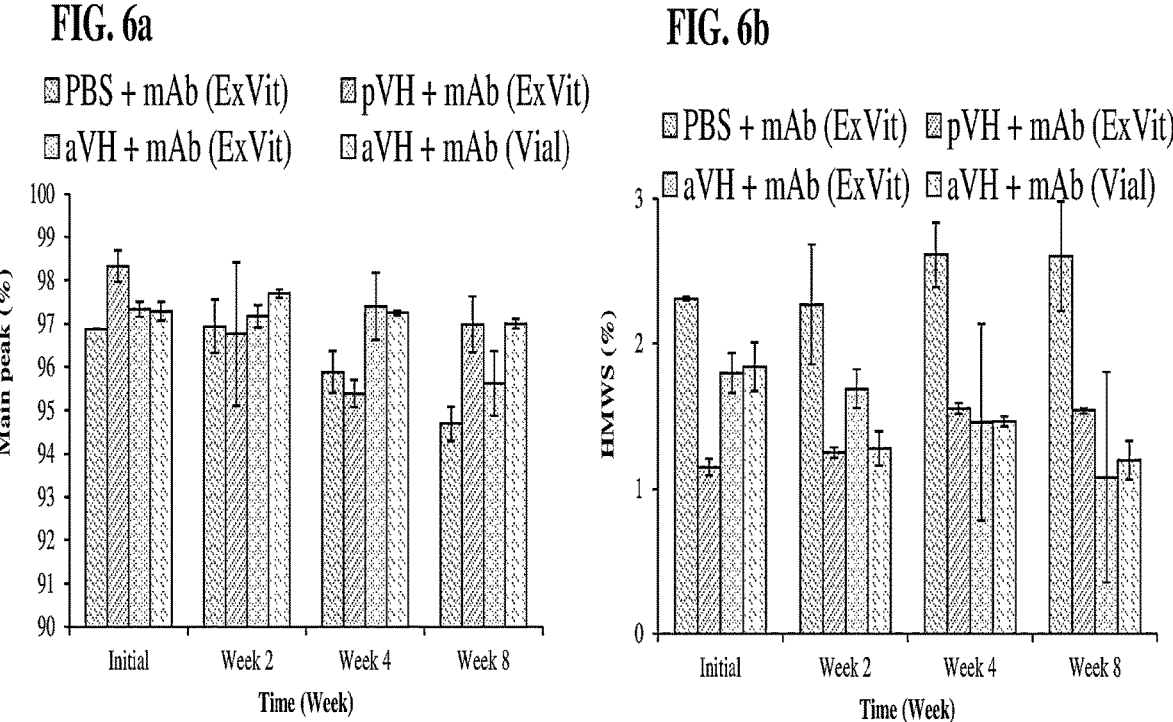
FIGS. 6a and 6b: Physical stability of mAb in aVH (ExVit or vial model), pVH and PBS were investigated by SEC.

Formation of soluble aggregates, although not experimentally proven, may have an impact on the safety and/or efficacy of protein drug. SEC results in FIGS. 6a and 6b demonstrate no change in the monomer content of mAb following 2 months of incubation in the Test-B and C. This is an interesting finding suggesting that mAb does not generate high molecular weight species (HMWS, soluble aggregates) and low molecular weight species (LMWS, fragments) in the pVH (Test-B) and also in the aVH when incubated in the vial (Test-C). On the other hand, significant loss in the main peak (2.3%) was observed when mAb was incubated in the PBS (Control-A) at 37° C. for the same amount of time. Surprisingly, Test-A showed minor loss in main peak at 2 month time point when compared with Test-C. In Test-C (Vial model), mAb is exposed only to the PBS present in aVH as buffer system, whereas in Test-A (ExVit model) mAb is exposed additionally to the PBS present in buffer-compartment as well. This may explain marginally higher loss in main peak observed in Test-A compared to Test-C.

Figures 7A, 7B:
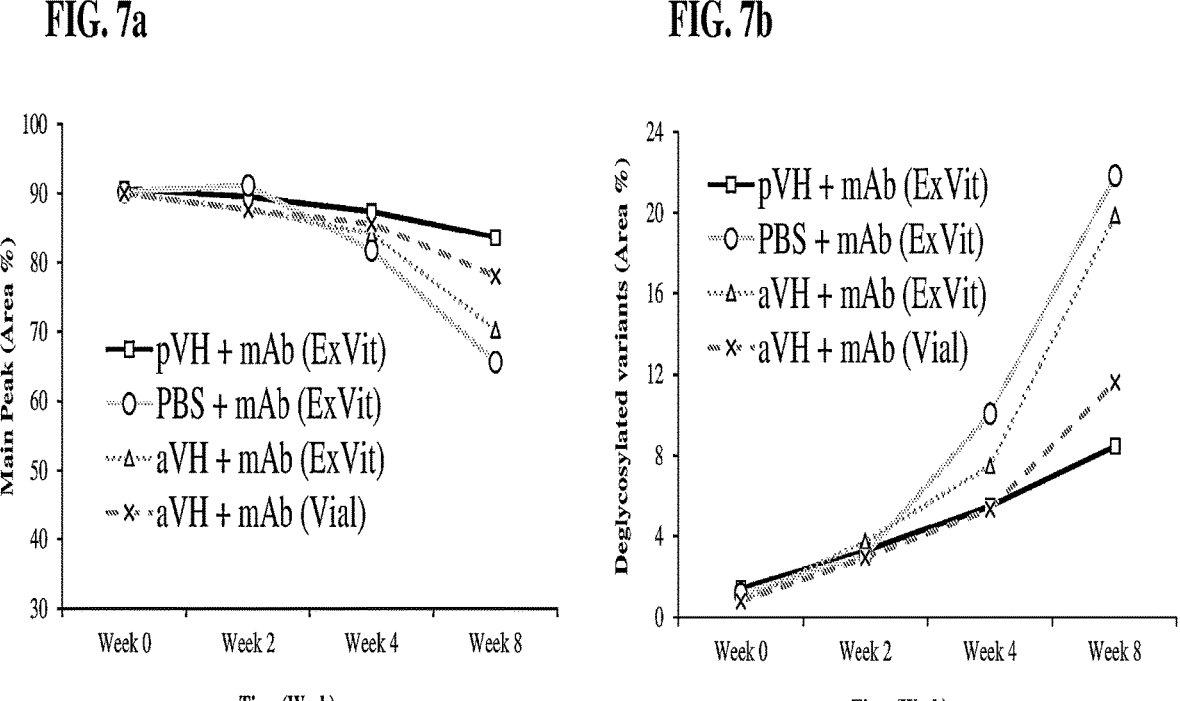
FIGS. 7a and 7b: Physical stability of mAb in aVH (ExVit or vial model), pVH and PBS was investigated by CE-SDS-NGS.

CE-SDS-NGS analysis was performed to evaluate physical stability and to assess mainly fragmentation of mAb after incubation in the PBS and VH at 37° C. Results depicted in FIG. 7, demonstrate the loss of a main peak area (FIG. 7a) and concurrent increase in smaller molecular weight deglycosylated variants (FIG. 7b). Loss of the main peak was ca. 25% in the Control-A group which was ca. 400% higher than the loss observed in the Test-B (ca. 7%). Moreover, the area of the LMWS for the control sample was increased more than 300% compared to the Test-B. Similarly as observed in the SEC, mAb incubated in the aVH with ExVit setup (Test-A) showed higher loss in the main peak and increase in the LMWS compared to the mAb incubated in the aVH with vial setup (Test-C). Moreover, physical stability of mAb in Test-A resembles more to the Control-A and physical stability of mAb in Test-C aligns more to the Test-B. It further confirms the results observed during SEC analysis. It is important to note that the LMWS observed in the Test-A, Test-B and Test-C are of the similar type which further supports the argument of using aVH in place of natural VH to predict in-vivo protein stability.

Example 10

Evaluation of Binding Affinity of mAb in the aVH and Natural VH

The specific interaction of mAb stability samples with their target antigens was assessed using a SPR-Biacore T100/T200 instrument (GE Healthcare). The dual binding SPR assay was conducted to evaluate the interactions between the mAb and its target antigens. The SPR assay was performed according to European Pharmacopoeia, Osmolality, Section 2.2.35, European Directorate for the Quality of Medicine, Strasbourg, France, 2017, pp. 59, which is herein incorporated by reference in its entirety. Capturing anti-human Fab antibody (Human Fab Capture Kit, GE Healthcare) was immobilized on a Biacore CM5-biosensor chip via standard amine coupling to achieve a coupling density of >5000 RU. Analysis was conducted at 25° C. and a flow rate of 10 μL/min using PBS-T (phosphate buffered saline containing 0.05% polysorbate 20, pH 7.4) as running and dilution buffer. The mAb stability samples (extracted from aVH/pVH/PBS) were injected on the measurement cell at various concentrations (13.85/19.04/26.18/36.00 μg/mL) for 90 s. Antigen-1 was injected for 60 s at a concentration of 0.5 μg/mL followed by an injection of 2.5 μg/mL Antigen-2 for 60 s on both (measurement- and reference-) flow cells, complex stability of both antigens was monitored for 30 s. Afterwards, the chip surface was regenerated by a 60 s injection of 10 mM pH 2.1 glycine solution at a flow rate of 30 μg/mL. Relative binding levels of the antigens to captured mAb samples were adjusted by normalization of the mAb sample capture level relative to the reference material with a defined activity of 100%. The obtained relative activity of the individual binding domains to their respective antigens was plotted against the incubation time.

Figure 8A:
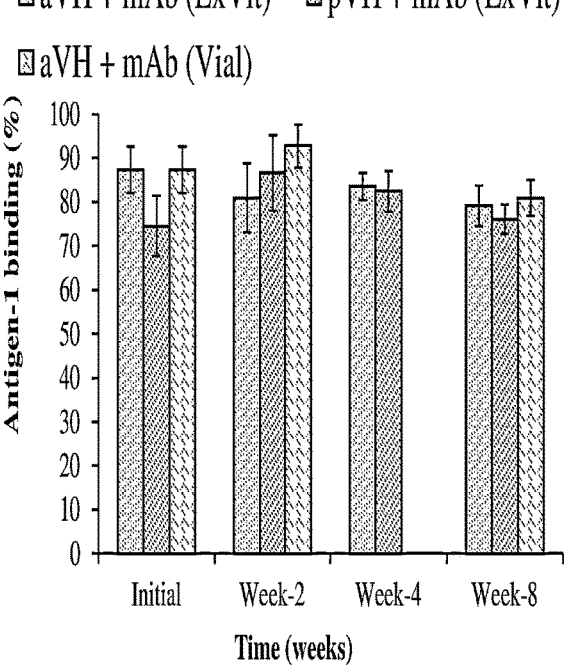
FIGS. 8a and 8b: Binding affinity of mAb.
Figure 8B:
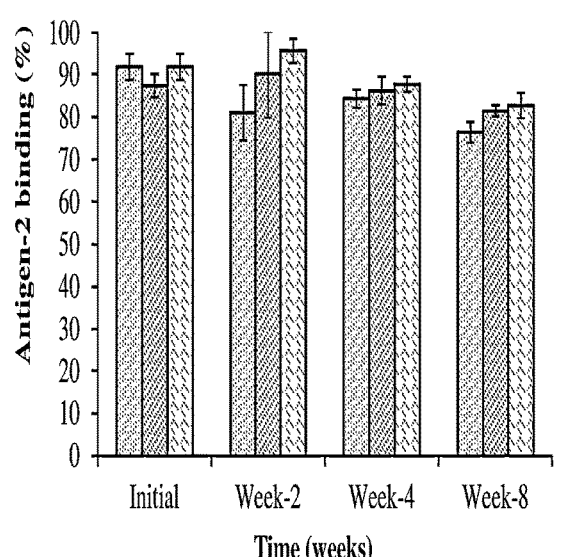

As shown in FIGS. 8a and 8b, a significant loss in the binding affinity of mAb to antigen-1 (20% loss) and antigen-2 (10% loss), respectively was observed in Test groups A, B and C. Though there was a difference observed in the physical stability of mAb in Test groups A, B and C, the loss in the binding affinity was not significantly different between these groups. It may be due to the fact that chemical alteration in the CDR of the antibody has direct impact on its binding affinity towards the antigen. The chemical stability of this mAb is highly impacted by environmental factors such as pH and temperature. In the stability study, pH and temperature were constant in all the groups throughout the study period. Hence, chemical stability of mAb in all the groups might get impacted equally and thus binding affinity of the mAb was also impacted similarly.

Example 11

Preparation of Small Molecule (SM) Active Pharmaceutical Ingredient (API)-Loaded PLGA Implants and In-Vitro Release of API from Long-acting Delivery (LAD) Implants in the aVH These LAD implants are produced by hot-melt extrusion process, very similarly to the marketed product Ozurdex which is comprised of Dexamethasone as SM API and PLGA as matrix forming polymer. The SM-loaded poly (lactic-co-glycolic acid (PLGA) implants were prepared using already established in house hot-melt extrusion protocol. Briefly, four different implants (F-1, F-2, F-3 and F-4) were prepared using hot-melt extrusion. These implants were varying in polymer type (hydrophobicity and end cap), polymer molecular weight, and extrusion temperature. Detailed composition and process parameters of implants are depicted in Table 11. To prepare implants, polymer and API were homogenously mixed and extruded at two different temperatures (F-1 and F-2 at 90° C., and F-3 at 110° C.). Further, to understand the impact of sterilization on the quality of implant, a part of F-3 batch was sterilized (F-4) using E-beam sterilization method. E-beam sterilization was performed at a standard target dose of 25 kGy, at room temperature using simultaneous beam processing 10 MeV, 20 KW linear accelerators Mevex (Ottawa, CN). All the implants were then immediately stored at 2-8° C. until further use.

TABLE 11

Composition and process parameters of SM-loaded PLGA LAD implants

| Implants | D,L-Lactide/ Glycolide Ratio | End Group | MW (kDa) | % Drug Loading | Extrusion temp. | Sterilization |
|---|---|---|---|---|---|---|
| F-1 | 75:25 | Ester | 100 | 25 | 90 | No |
| F-2 | 75:25 | Acid | 30 | 25 | 90 | No |
| F-3 | 75:25 | Ester | 100 | 25 | 110 | No |
| F-4 | 75:25 | Ester | 100 | 25 | 110 | Yes (E-Beam) |

Figure 9:
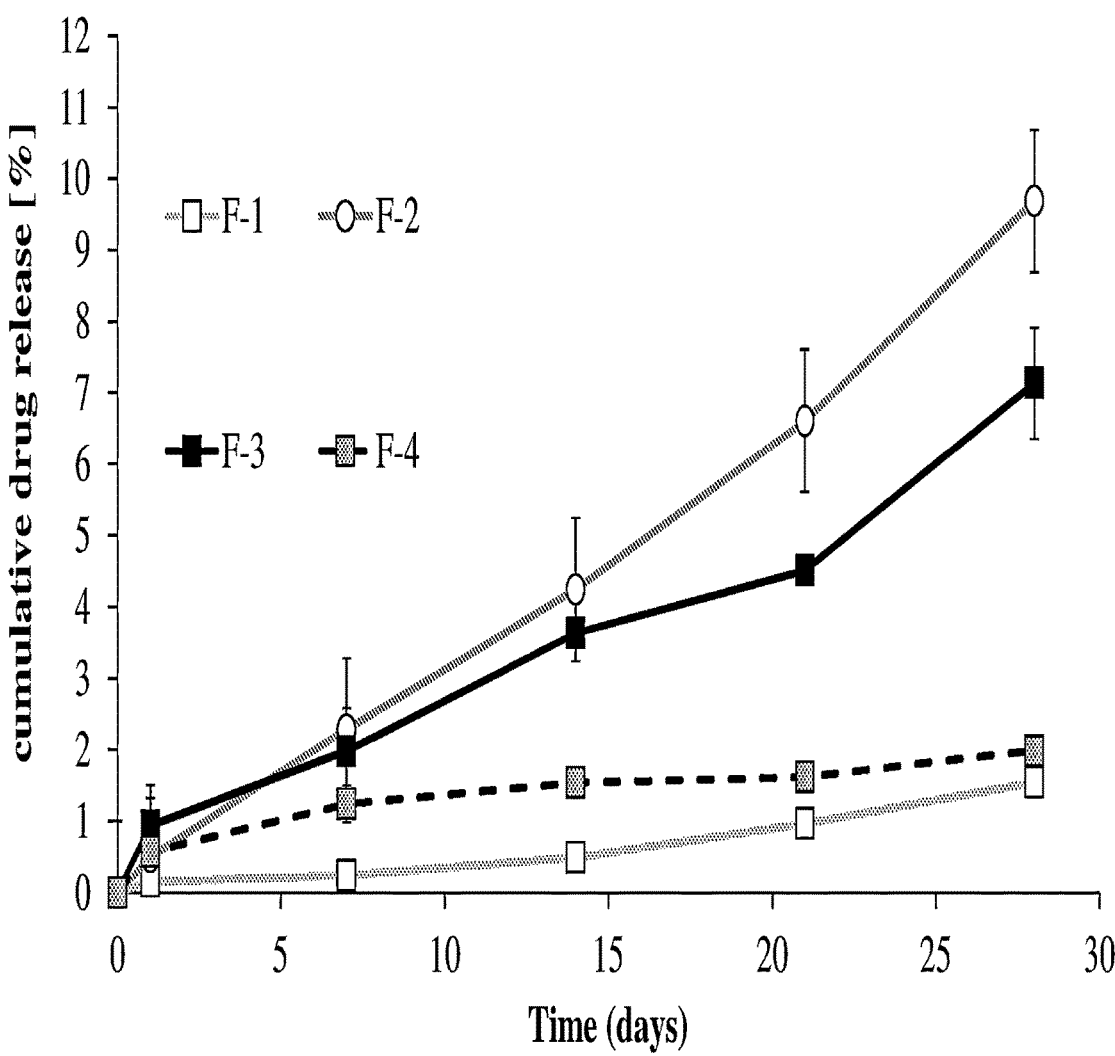
FIG. 9: Cumulative Release (%) of Small Molecule (SM) active pharmaceutical ingredients (API) from various PLGA based LAD intravitreal implants.

These implants were characterized for various key parameters such as quantity, homogeneity and stability of API following extrusion, and importantly for release of API. In-vitro and in-vivo release of API from LAD implants can be easily impacted by complex interdependent formulation and process variables. These parameters could be related to matrix forming polymer (such as MW of polymer, hydrophobicity of polymer, etc.), and/or API (hydrophobicity, physical state of API such as polymorph or salt forms), and/or related to processes (such as sterilization, extrusion temperature, etc.). To capture the impact of these variables on the release of API, it is very important to select the correct release medium. Therefore, the possibility of aVH to be used as a release medium for the LAD implants intended for intravitreal administration was evaluated. Briefly, a 5 mg of above different implants (F-1 to F-4) were incubated in 2 mL of an aVH for 4 weeks at 37° C. Samples were collected after 1, 7, 14, 21 and 28 days of incubation, and analyzed by HPLC method (developed in house) for the qualitative and quantitative estimation of SM. As depicted in FIG. 9, all the implants showed different levels of SM release after 4 weeks. Implant F-2 was comprised of fastest degrading polymer and hence it showed the fastest release compared to all other implants. Implants F-1 and F-3 were identical in composition but extruded at different temperature. F-3 exhibited significantly higher release compared to F-1. This difference in release might be attributed to the fact that F-3 is extruded above the Tg (96° C.) of API. The higher extrusion temperature may have resulted in homogeneous blending of hydrophobic drug with polymer which eventually leads to faster release of API. Whereas F-2 was extruded below the Tg of API and therefore API may have remained in its original particulate form leading to non-homogeneous mixing with polymer. Because API is hydrophobic, these API particles might have exhibited very poor dissolution and diffusion based release in an aVH. Interestingly, F-4 showed significantly slower release compared to F-3. It might possible that the process of e-beam sterilization has introduced structural changes in the biodegradable PLGA polymer which has resulted in slower release of API.

It is important to note that aVH as a release medium was able to differentiate the implants based on their key quality feature i.e., release of API. This experiment in aVH clearly enables to see differences between different types of polymers and also captures differences coming from processing such as temperature and sterilization. In other words, aVH as release medium is able to discriminate between formulations that are known to, or at least expected to perform differently. Hence, aVH can not only be used to investigate the stability of formulations (as highlighted in previous examples) but also can be used to investigate release of API from LAD formulations. Furthermore, aVH as disclosed herein can better mimic the in vivo conditions with regard to API release and/or drug release from LAD implants.

The invention claimed is:

1. A method for analyzing the behavior of a substance comprising the steps in order:
   (i) providing an artificial vitreous humor composition in an in vitro environment;
   (ii) applying the substance to the artificial vitreous humor; and
   (iii) determining at least one property of the applied substance,
   wherein the artificial vitreous humor composition comprises,
   (A) a phosphate buffer, wherein the phosphate buffer is phosphate buffer saline (PBS) in the range from 0.001 to 0.2 M and has a pH value in the range from 7.0 to 7.7, (B) 64.6 µM creatinine, 2.2 mM glucose, 7.6 mM urea, 580 µM xanthine, 309 µM hypoxanthine, 10.5 mM sodium lactate and 200 µM glutathione, and
   (C) 40 mg/L type II collagen and 0.6% w/v sodium hyaluronate, and
   wherein the applied substance is left in the artificial vitreous humor composition for up to 360 days, prior to step (iii) and the artificial vitreous humor composition remains at a pH having a value in the range from 7.0 to 7.7.

2. The method of claim 1, wherein the substance to be applied is at least one of a macromolecule, a drug formulation, an excipient, a protein or a combination thereof.

3. The method of claim 1, wherein the substance to be applied comprises molecules having a size in a range between 100 Da and 1800 kDa.

4. The method of claim 1, wherein the at least one property of the applied substance is selected from the group consisting of stability, bioavailability, release from drug-loaded long acting delivery (DDS) system and degradation of DDS system.

5. A method for analyzing the behavior of an artificial humor composition comprising the steps in order:
   (i) providing an artificial vitreous humor composition in an in vitro environment;
   (ii) applying a substance to the artificial vitreous humor; and
   (iii) determining at least one property of the artificial humor composition,
   wherein the artificial vitreous humor composition comprises,
   (A) a phosphate buffer, wherein the phosphate buffer is phosphate buffer saline (PBS) in the range from 0.001 to 0.2 M and has a pH value in the range from 7.0 to 7.7,
   (B) 64.6 µM creatinine, 2.2 mM glucose, 7.6 mM urea, 580 µM xanthine, 309 µM hypoxanthine, 10.5 mM sodium lactate and 200 µM glutathione, and
   (C) 40 mg/L type II collagen and 0.6% w/v sodium hyaluronate, and
   wherein the applied substance is left in the artificial vitreous humor composition for up to 360 days, prior to step (iii) and the artificial vitreous humor composition remains at a pH having a value in the range from 7.0 to 7.7.

* * * * *